United States Patent

Dannheim et al.

Patent Number: 5,430,147
Date of Patent: Jul. 4, 1995

[54] WATER-SOLUBLE ANTHRAQUINONE COMPOUNDS, PREPARATION THEREOF, AND USE THEREOF AS DYES

[75] Inventors: Jörg Dannheim, Franfurt am Main; Reinhard Hähnle, Königstein/Taunus; Werner H. Russ, Flösheim/Main, all of Germany

[73] Assignee: Hoechst AG, Frankfurt, Germany

[21] Appl. No.: 161,757

[22] Filed: Dec. 3, 1993

[30] Foreign Application Priority Data

Dec. 5, 1992 [DE] Germany .................. 42 41 035.5
Jun. 22, 1993 [DE] Germany .................. 43 20 562.3

[51] Int. Cl.6 ............... C09B 62/06; C07D 251/00
[52] U.S. Cl. ..................... 544/189; 8/549; 8/676; 8/677; 8/679; 8/917; 8/918; 8/924
[58] Field of Search ........................ 544/189

[56] References Cited

U.S. PATENT DOCUMENTS

| | | | |
|---|---|---|---|
| 4,273,553 | 6/1981 | Harms et al. | 544/189 |
| 4,325,705 | 4/1982 | Harms et al. | 544/189 |
| 4,394,129 | 7/1983 | Springer | 8/543 |
| 4,503,224 | 3/1985 | Harms et al. | 544/189 |
| 4,507,476 | 3/1985 | Niwa et al. | 544/189 |
| 4,550,203 | 10/1985 | Stockinger et al. | 564/105 |
| 4,631,341 | 12/1986 | Kayane et al. | 544/189 |
| 4,837,320 | 6/1989 | Harms et al. | 544/189 |
| 4,851,528 | 7/1989 | Stead et al. | 544/189 |
| 5,112,971 | 5/1992 | Akahuri et al. | 544/189 |
| 5,231,172 | 7/1993 | Beck et al. | 544/189 |
| 5,268,457 | 12/1993 | Tzikas | 544/189 |
| 5,274,083 | 12/1993 | Herd et al. | 544/189 |

FOREIGN PATENT DOCUMENTS

| | | |
|---|---|---|
| 24676 | 3/1981 | European Pat. Off. |
| 87394 | 8/1983 | European Pat. Off. |
| 57-199878 | 12/1982 | Japan |
| 63-072668 | 4/1988 | Japan |

OTHER PUBLICATIONS

Feiccabrina et al. CA81 (17): 1056494 (1974).
Patent Abstracts of Japan, vol. 12, No. 301 (C-521)(3148) Aug. 16, 1988.

*Primary Examiner*—Cecilia Tsang
*Attorney, Agent, or Firm*—Connolly and Hutz

[57] ABSTRACT

Water-soluble anthraquinone compounds, preparation thereof, and use thereof as dyes.

There are described anthraquinone compounds conforming to the formula (1)

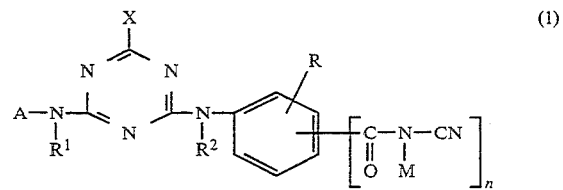

where
A is the radical of a sulfo-containing anthraquinone radical,
$R^1$ and $R^2$ are each independently of the other hydrogen or lower alkyl,
X is an alkali-detachable radical, such as fluorine and chlorine,
R is hydrogen, lower alkyl or lower alkoxy, and
M is hydrogen or an alkali metal.

The anthraquinone compounds have fiber-reactive properties and are used as dyes for dyeing and printing hydroxy- and/or carboxamido-containing material, in particular fiber material, for example cellulose fiber materials, wool and synthetic polyamide, in brilliant blue shades.

12 Claims, No Drawings

WATER-SOLUBLE ANTHRAQUINONE COMPOUNDS, PREPARATION THEREOF, AND USE THEREOF AS DYES

The invention relates to the field of fiber-reactive dyes.

Japanese Patent Application Publication Sho-57-199 878 discloses inter alia anthraquinonoid dyes containing cyanamido, N-cyanobenzamido and N-cyanosulfonamido groups. However, they have some application defects, such as low degrees of fixation, low color strength and lack of brilliance.

The present invention now provides anthraquinone compounds which when used as fiber-reactive dyes are advantageous over the known dyes and produce dyeings of high color strength in brilliant blue shades. The new anthraquinone compounds conform to the formula (1)

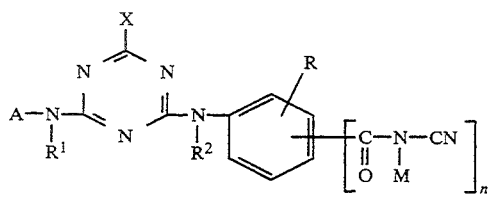

where
- A is the radical of a sulfo-containing anthraquinone radical, in particular the radical of a dye having a customary anthraquinone chromophore,
- $R^1$ is hydrogen or alkyl of 1 to 4 carbon atoms, such as methyl and ethyl, preferably hydrogen,
- $R^2$ is hydrogen or alkyl of 1 to 4 carbon atoms, such as methyl and ethyl, preferably hydrogen,
- X is an alkali-detachable radical, for example fluorine, chlorine, bromine, methylsulfonyl, preferably chlorine and fluorine,
- R is hydrogen, alkyl of 1 to 4 carbon atoms, such as ethyl and in particular methyl, or alkoxy of 1 to 4 carbon atoms, such as ethoxy and in particular methoxy,
- n is 1 or 2,
- M is hydrogen or an alkali metal, such as sodium, potassium and lithium, or the mole equivalent of an alkaline earth metal, such as calcium, but not the below-indicated compounds of the formulae (A-1) and (A-2)

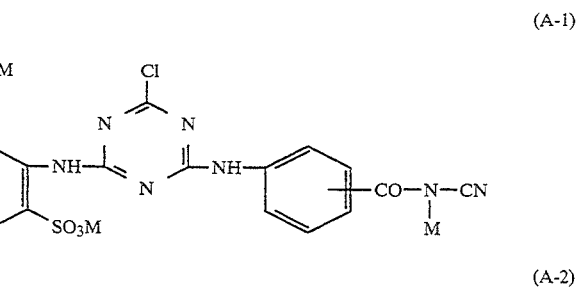

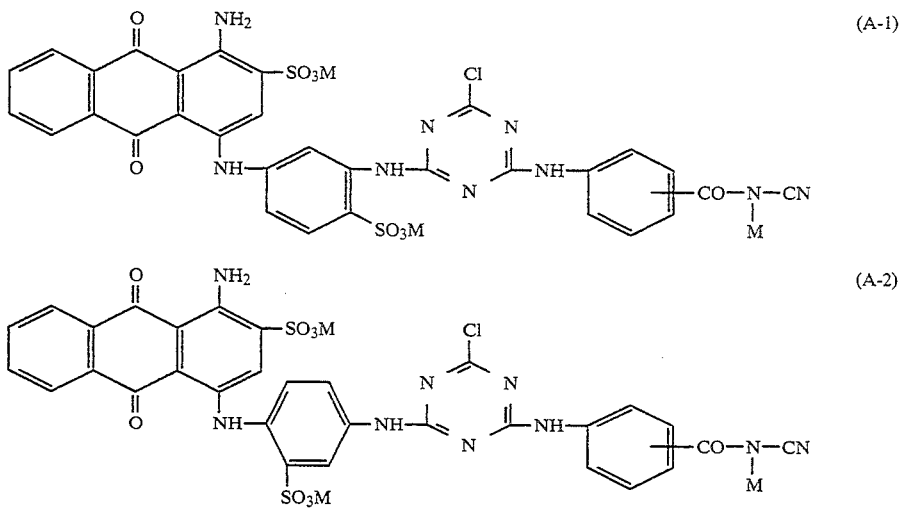

where M is as defined above.

In addition to one or more sulfo groups, the radical A can contain further substituents, for example alkyl of 1 to 4 carbon atoms, such as methyl, ethyl, propyl, isopropyl and butyl, alkoxy of 1 to 4 carbon atoms, such as methoxy, ethoxy, propoxy, isopropoxy and butoxy, alkanoylamino of 2 to 5 carbon atoms, such as acetylamino and propionylamino, benzoylamino, carboxy-, $C_1$-$C_4$-alkyl-, $C_1$-$C_4$-alkoxy- and/or sulfo-substituted benzoylamino, halogen, such as fluorine, chlorine and bromine, nitro, cyano, trifluoromethyl, sulfamoyl, carbamoyl, ureido, hydroxy, carboxy and sulfomethyl.

Preferably the radical A is a radical of the formula (2)

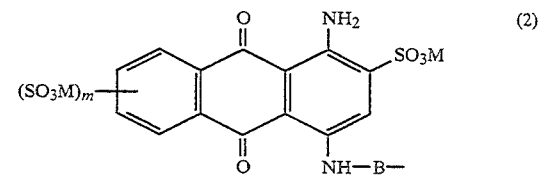

where
- M is as defined above,
- m is zero, 1 or 2 (when zero, the group in question is hydrogen), preferably zero or 1, and particularly preferably zero,
- B is phenylene which can be substituted by 1 to 4 substituents selected from the group of substituents consisting of 2 sulfo, 1 carboxy, 4 alkyl of 1 to 4 carbon atoms, such as ethyl and in particular methyl, and 2 alkoxy of 1 to 4 carbon atoms, such as ethoxy and in particular methoxy; or is alkylene of 1 to 4 carbon atoms, such as propylene and ethylene, or is phenylenealkylene or alkylenephenylene, wherein the alkylene radicals have 1 to 4 carbon atoms and the phenylene radicals are unsubstituted or substituted by 1, 2 or 3 substituents from alkyl of 1 to 4 carbon atoms, such as ethyl and in particular methyl, alkoxy of 1 to 4 carbon atoms, such as ethoxy and in particular methoxy, and sulfo, or is ($C_5$-$C_8$) cycloalkylene or alkylene($C_5$-$C_8$)cycloalkylene or ($C_5$-$C_8$)cycloalkylenealkylene or alkylene($C_5$-$C_8$)-cycloalkylenealkylene, wherein the cycloalkylene radicals, such as cyclohexylene radicals, may additionally be substituted by 1 or 2 methyl groups and the alkylene radicals are those of 1 to 4 carbon atoms, or is a radical of the formula -phen-D-phen-, 30 in which each phen is identical to or different from the other, is phenylene, preferably para-phenylene, which is unsubstituted or substituted by 1 or 2 substituents from the group consisting of sulfo, alkyl of 1 to 4 carbon atoms, such as ethyl and in particular methyl, alkoxy of 1 to 4 carbon atoms, such as ethoxy and in particular methoxy, and D is a direct bond or a group of the formula —NH—, —O—, —$SO_2$—, —CO—NH—, —NH—CO—, —$SO_2$—NH—, —NH—$SO_2$— and —$SO_2$—NH—$SO_2$—.

Radicals of the formula (2) include for example 1-amino-2-sulfoanthraquinone-4-amino-(3'-sulfo-2',4',6'-trimethyl)phen-5'-yl, 1-amino-2-sulfoanthraquinone-4-amino- (3'-sulfo)phen-4'-yl, 1-amino-2,7-disulfoanthraquinone-4-amino-(3'-sulfo) phen-4'-yl, 1-amino-2,6-disulfoanthraquinone-4-amino-(3'-sulfo)phen-4'-yl, 1-amino-2,7-disulfoanthraquinone-4-amino-(4'-sulfo)-phen-3'-yl, 1-amino-2,6-disulfoanthraquinone-4-amino-(4'-sulfo) phen-3'-yl, 1-amino-2-sulfoanthraquinone-4-amino-(4'-sulfo)phen-3'-yl, 1-amino-2-sulfoanthraquinone-4-amino-(2',4'-disulfo) phen-5'-yl, 1-amino-2-sulfoanthraquinone-4-amino-(3',2''-disulfo)diphen(4',1'')-4''-yl, 1-amino-2-sulfoanthraquinone -4-amino-(3''-sulfo)diphen -(4',1'')-4''-yl, 1-amino-2-sulfoanthraquinone-4-amino-(2'-sulfo)phenyl-4'-methyl, 1-amino-2,6-disulfoanthraquinone-4-amino-(2'-sulfo)phen-4'-yl, 1-amino-2-sulfoanthraquinone-4-aminocyclohex-4'-yl, 1-amino-2,7-disulfoanthraquinone-4-amino-(2'-sulfo)phen-4'-yl, 1-amino-2,5-disulfoanthraquinone-4-amino-(2'-sulfo)-phen-4'-yl, 1-amino-2,8-disulfoanthraquinone-4-amino-(2'-sulfo)phen-4'-yl, 1-amino-2,6-disulfoanthraquinone-4-amino-(2'-sulfo)phen-3'-yl, 1-amino-2,7-disulfoanthraquinone-4-amino-(2'-sulfo)phen-3'-yl, 1-amino-2-sulfoanthraquinone-4-amino-(4'-methyl)cyclohex-3'-yl, 1-amino-2-sulfoanthraquinone -4-amino-(2'-sulfo) phenyl -5'-methyl, 1-ammino-2-sulfoanthraquinone-4-amino-(2'-sulfo-4'-methoxy)phenyl-5'-methyl , 1-amino-2-sulfoanthraquinone-4- amino-(2'-sulfo-6'-methoxy)-phenyl-3'-methyl, 1-amino-2-sulfoanthraquinone -4-amino-(3' -sulfo -2 ',6'- dimethyl)phenyl-5'-methyl, 1-amino-2-sulfoanthraquinone -4-amino-(2'-sulfo -4'- methyl) phenyl -6'-methyl, 1-amino-2,6-disulfoanthraquinone-4-amino-(2'-sulfo-4'-methyl)phenyl-6'-methyl, 1-amino-2-sulfoanthraquinone-4-amino-(2'-sulfo-6'-methyl)phen-4'-yl, 1-amino-2-sulfoanthraquinone-4-amino-(4'-sulfo-6'-methyl)phen-3'-yl, 1-amino-2-sulfoanthraquinone-4-amino-(3'-sulfo-2',4',6'-trimethyl)-phenyl-5'-methyl, 1-amino-2,6-disulfoanthraquinone-4-amino-(3'-sulfo-6'-methyl)phen-5'-yl, 1-amino-2-sulfoanthraquinone-4-amino-(3'-sulfo-6'-methyl)phen-5,-yl, 1-amino-2,5-disulfoanthraquinone-4-amino-(6'-methyl)phen-5'-yl, 1-amino-2,6-disulfoanthraquinone-4-amino-(6'-methyl)phen-5'-yl, 1-amino-2,5,8-trisulfoanthraquinone-4-aminophen-4'-yl, 1-amino-2,6-disulfoanthraquinone-4-aminophen-4'-yl, 1-amino-2,7-disulfoanthraquinone-4-aminophen-4,-yl, 1-amino-2,5-disulfoanthraquinone-4-aminophen-4'-yl, 1-amino-2,6-disulfoanthraquinone-4-aminophen-3'-yl, 1-amino-2,5-disulfoanthraquinone-4-aminophen-3'-yl, 1-amino-2,6-disulfoanthraquinone-4-amino-(3'-sulfo-2',6'-dimethyl)phenyl-5'-methyl, 1-amino-2,7-disulfoanthraquinone-4-amino-(3'-sulfo-2',6'-dimethyl)phenyl-5'-methyl, 1-amino-2,5-disulfoanthraquinone-4-amino.(2'-sulfo-4'-methyl)phenyl-3'-methyl, 1-amino-2,8-disulfoanthraquinone-4-amino-(4'-methyl)phenyl-3'-methyl, 1-amino-2,5,8-trisulfoanthraquinone-4-amino-(2',6'-dimethyl)phenyl-3'-methyl, 1-amino-2,8-disulfoanthraquinone-4-amino-(2'-sulfo)phenyl-3'-methyl, 1-amino-2,7-disulfoanthraquinone-4-amino-(2'-sulfo-4'-methoxy)phenyl-3'-methyl, 1-amino-2,5-disulfoanthraquinone-4-amino-(3'-sulfo)phen-4'-yl, 1-amino-2,5-disulfoanthraquinone-4-amino-(3'-sulfo-6'-methyl)phen-5'-yl, 1-amino-2,7-disulfoanthraquinone-4-aminoeth-2'-yl, 1-amino-2-sulfoanthraquinone-4-aminophen-3'-yl-1''-sulfonylamidosulfonyl-4''-sulfophen-3''-yl, 1-amino-2,6-disulfoanthraquinone-4-aminophen-4'-yl-1''-sulfonylamidosulfonylphen-4''-yl and 1-amino-2-sulfoanthraquinone-4-aminophen-3'-yl-1''-sulfonylamidosulfonylphen-3''-yl, preferably 1-amino-2-sulfoanthraquinone-4 -amino-(2',4',6'- trimethyl -5'-sulfo) phen-3-yl and 1-amino-2-sulfoanthraquinone-4-amino-(4'-sulfo) phen -3'-yl.

Of the anthraquinone compounds of the formula (1) according to the invention, attention may be drawn in particular to those which conform to the formulae (3a) and (3b)

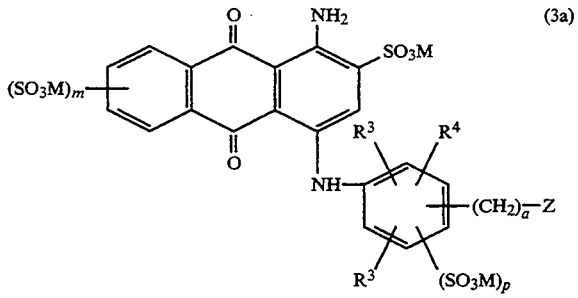

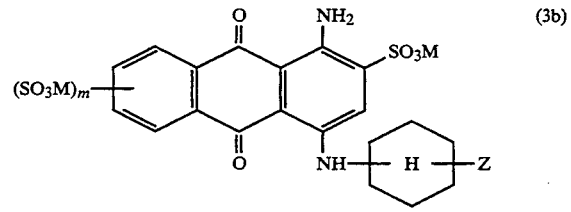

where

M and m each have one of the abovementioned meanings, in particular one of the preferred meanings, $R^3$ is hydrogen or alkyl of 1 to 4 carbon atoms, such as ethyl and in particular methyl, $R^4$ is hydrogen or alkyl of 1 to 4 carbon atoms, such as ethyl and in particular methyl, $R^5$ is hydrogen or alkyl of 1 to 4 carbon atoms, such as ethyl and in particular methyl, p is zero, 1 or 2, preferably 1 (when zero, the group in question being hydrogen), a is zero or 1, preferably zero, and Z is a radical of the formula (4)

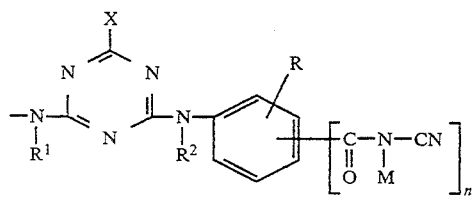           (4)

where $R^1$, $R^2$, R, M, n and X each have the abovementioned meanings, in particular the preferred meanings, and X is particularly preferably chlorine or fluorine, especially chlorine.

In the formula (3a) the symbols $R^3$, $R^4$ and $R^5$ are each preferably methyl.

Of these preferred anthraquinone compounds particular preference is given to those which conform to the formula (5)

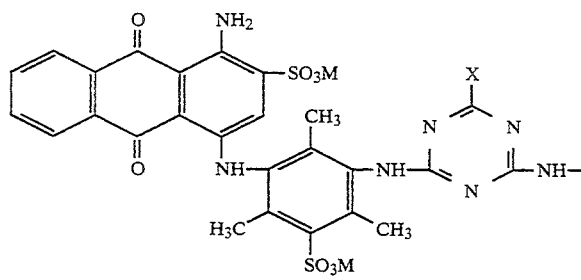           (5)

where M, R and n each have one of the abovementioned meanings, in particular one of the preferred meanings, X is chlorine or fluorine, preferably chlorine, n is preferably 1, and the cyanamidocarbonyl group on the benzene ring is meta or para to the —NH— group.

The present invention further provides a process for preparing the anthraquinone compounds of the formula (1) according to the invention, which comprises reacting a halo-s-triazine compound of the formula (6)

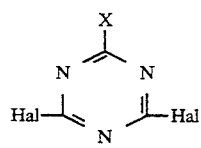           (6)

where X has one of the abovementioned meanings, in particular one of the preferred meanings, and Hal is halogen, such as chlorine or fluorine, for example 2,4,6-trifluoro-1,3,5-triazine (cyanuric fluoride) or 2,4,6-trichloro-1,3,5-triazine (cyanuric chloride), with an amino-containing anthraquinone compound of the formula A—$NHR^1$, where A and $R^1$ each have one of the abovementioned meanings, in particular one of the preferred meanings, and with an amino compound of the formula (7)

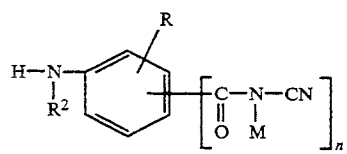           (7)

where $R^2$, R, M and n are each as defined above, in any desired order.

Variants of the process according to the invention which are likewise according to the invention comprise for example reacting a compound of the formula (8)

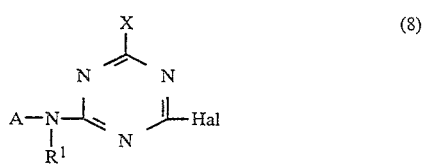           (8)

in which A, $R^1$, X and Hal are each as defined above, with an amino compound of formula (7), or a compound of the formula (9)

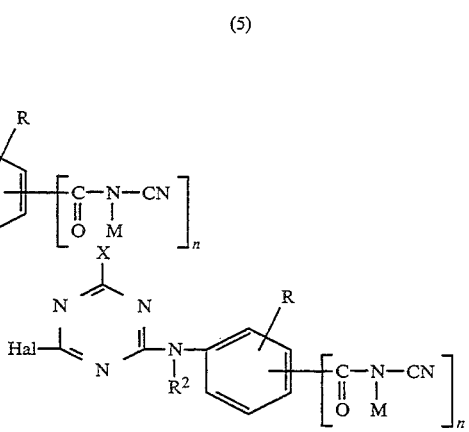           (9)

where Hal, X, $R^2$, R, M and n are each as defined above, with a compound of the formula A—$NHR^1$ where A and $R^1$ are each as defined above. Of these, the variant whereby a compound of the formula (8) is reacted with a compound of the formula (7) is preferred.

The reactions of the starting compounds are carried out in an aqueous or aqueous-organic medium in suspension or solution. If the reactions are carried out in an aqueous-organic medium, the organic medium will be for example acetone, dimethylformamide, dimethyl sulfoxide or N-methylpyrrolidone. Advantageously, the hydrogen halide liberated in the course of the condensation is continuously neutralized by the addition of aqueous alkali metal hydroxides, carbonates or bicarbonates. The first condensation reaction of the halo-s-triazine of the formula (6) is in general carried out at a temperature between −5° C. and +20° C., in the case of Hal being fluorine preferably at a temperature of between −5° C. and +5° C., and at a pH between 2 and 10, preferably between 4 and 6. The subsequent condensation reaction with the second amino compound is in general carried out at a temperature between 5° and 40° C., in the case of Hal being fluorine preferably at a temperature between 0° and 20° C., and at a pH between 3 and 9, preferably between 6 and 7.

More particularly, the reaction between a compound of the formula (8) and a compound of the formula (7) is carried out at a temperature between 5° and 40° C., preferably between 10° and 30° C., and at a pH between 3 and 9, preferably between 6 and 7, although when in the compound of the formula (8) Hal is a fluorine atom the reaction is preferably carried out at a temperature between 0° and 20° C.

Similarly, the reaction of a compound of the formula (9) with a compound of the formula A—NHR$^1$ is carried out at a temperature between 5° and 40° C., preferably between 10° and 30° C., and at a pH between 3 and 9, preferably between 4 and 6, although when Hal in the compound of the formula (9) is fluorine the reaction is preferably carried out at a temperature between 0° and 20° C.

The starting compounds of the formula (8) can be prepared in a conventional manner of reacting halogen-substituted triazines with amino-containing compounds, as described for example above for the procedures of the invention, for instance likewise in aqueous or aqueous-organic medium in general at a temperature between −5° C. and 40° C., preferably between 0° and 30° C., and at a pH between 2 and 10, preferably between 5 and 7, although when Hal in the starting compound of the formula (6) is fluorine the reaction temperature is preferably between −5° C. and 5° C. The same method and conditions can be used to prepare the starting compounds of the formula (9) by reacting a compound of the formula (6) with a compound of the formula (7).

The starting compounds of the formula (6) and of the formula A—NHR$^1$ are generally known and have been numerously described in the literature. Compounds of the formula (6) include for example cyanuric chloride and cyanuric fluoride.

Starting compounds of the formula A—NHR$^1$ include for example 1-amino-2-sulfo-4-(3'-sulfo-2',4',6'-trimethyl-5'-aminophenyl)aminoanthraquinone, 1-amino-2-sulfo-4-(3'-sulfo-4'-aminophenyl)aminoanthraquinone, 1-amino-2,7 -disulfo-4-(3'-sulfo-4'-aminophenyl)aminoanthraquinone, 1-amino-2,6-disulfo-4-(3'-sulfo-4'-aminophenyl)aminoanthraquinone, 1-amino-2,7-disulfo-4-(4'-sulfo-3'-aminophenyl)aminoanthraquinone, 1-amino-2,6-disulfo-4-(4'-sulfo-3'- aminophenyl)aminoanthraquinone, 1-amino-2-sulfo-4-(4'-sulfo-3'-aminophenyl)aminoanthraquinone, 1-amino-2-sulfo-4-(2',4'-disulfo-5'-aminophenyl)aminoanthraquinone, 1-amino-2-sulfo-4-[3',2''-disulfo-4''-aminodiphenyl-(4',1'')]aminoanthraquinone, 1-amino-2-sulfo-4-[3''-sulfo-4''-aminodiphenyl(4',1'')]aminoanthraquinone, 1-amino-2-sulfo-4-(2'-sulfo-4'-aminomethylphenyl)aminoanthraquinone, 1-amino-2-sulfo-4-[2'-sulfo-4'-(N-methylamino)methylphenyl]aminoanthraquinone, 1-amino-2,6-disulfo-4-(2'-sulfo-4'-aminophenyl)aminoanthraquinone, 1-amino-2-sulfo-4-(4'-aminocyclohexyl)aminoanthraquinone, 1-amino-2,6-disulfo-4-(4'-aminocyclohexyl)aminoanthraquinone, 1-amino-2,7-disulfo-4-(4'-aminocyclohexyl)aminoanthraquinone, 1-amino-2,5-disulfo-4-(4'-aminocyclohexyl)aminoanthraquinone, 1-amino-2,8-disulfo-4-(4'-aminocyclohexyl)aminoanthraquinone, 1-amino-2,7-disulfo-4-(4 '-methylaminocyclohexyl) aminoanthraquinone, 1-amino-2,6disulfo-4-(3'-aminocyclohexyl)aminoanthraquinone, 1-amino-2,7-disulfo-4-(3'- aminocyclohexyl)aminoanthraquinone, 1-amino-2-sulfo-4-(4'-methyl-3'-aminocyclohexyl)aminoanthraquinone, 1-amino-2-sulfo-4-[2'-sulfo-4'-(N-methylamino) methylphenyl]aminoanthraquinone, 1-amino-2-sulfo-4-(2'-sulfo-5'-aminomethylphenyl)aminoanthraquinone, 1-amino-2-sulfo-4-[2'-sulfo-5'-(N-methylamino)methylphenyl]aminoanthraquinone, 1-amino-2-sulfo-4-(2'-sulfo-4'-methoxy -5'- aminomethylphenyl)aminoanthraquinone, 1-amino-2-sulfo-4-[2'-sulfo-4'-methoxy-5'-(N-methylamino)methylphenyl]aminoanthraquinone, 1-amino-2-sulfo-4-(2'-sulfo-6'-methoxy-3'-aminomethylphenyl)aminoanthraquinone, 1-amino-2-sulfo-4-(3'-sulfo-2',6'-dimethyl-5'-aminomethylphenyl)aminoanthraquinone, 1-amino-2-sulfo-4-(2'-sulfo-4'-methyl-6'-aminomethylphenyl)aminoanthraquinone, 1-amino-2-sulfo-4-[2'-sulfo-4'-methyl-6'-(N-methylamino)methylphenyl]aminoanthraquinone, 1-amino-2,6-disulfo-4-[2'-sulfo-4'-methyl-6'-aminomethylphenyl] aminoanthraquinone, 1-amino-2-sulfo-4-(2'-sulfo-6'-methyl-4 '-aminophenyl)aminoanthraquinone, 1-amino-2-sulfo-4-(4'-sulfo-6'- methyl-3'-aminophenyl)aminoanthraquinone, 1-amino-2-sulfo-4-(3'-sulfo-2',4',6'-trimethyl-5'-aminomethylphenyl)aminoanthraquinone, 1-amino-2,6-disulfo-4-(3'-sulfo-6'-methyl-5'-aminophenyl)aminoanthraquinone, 1-amino-2-sulfo-4-(3'-sulfo-6'-methyl-5'-aminophenyl)aminoanthraquinone, 1-amino-2,5-disulfo-4-(6'-methyl-5'-aminophenyl)aminoanthraquinone, 1-amino-2,6-disulfo-4-(6'-methyl-5'-aminophenyl)aminoanthraquinone, 1-amino-2,5,8-trisulfo-4-(4'-aminophenyl)aminoanthraquinone, 1-amino-2,6-disulfo-4-[2'-sulfo-4'-(N-methylamino)methylphenyl]aminoanthraquinone, 1-amino-2,7-disulfo-4-[2'-sulfo-4'-(N-methylamino)methylphenyl]aminoanthraquinone, 1-amino-2,5,8-trisulfo-4-[4'-(N-methylamino)methylphenyl]aminoanthraquinone, 1-amino-2,8-disulfo-4-[4'-(N-methylamino)methylphenyl]aminoanthraquinone, 1-amino-2,6-disulfo-4-(4'-aminophenyl)aminoanthraquinone, 1-amino-2,7-disulfo-4-(4'-aminophenyl)aminoanthraquinone, 1-amino-2,5-disulfo-4-(4'-aminophenyl)aminoanthraquinone, 1-amino-2,6-disulfo-4-(3'- aminophenyl)aminoanthraquinone, 1-amino-2,5-disulfo-4-(3'-aminophenyl)aminoanthraquinone, 1-amino-2,6-disulfo-4-(3'-sulfo-2',6'-dimethyl-5'-aminomethylphenyl)aminoanthraquinone, 1-amino-2,6-disulfo-4-[3'-sulfo-2',6'-dimethyl-5'-(N-methylamino)methylphenyl-1]aminoanthraquinone, 1-amino-2,7-disulfo-4-(3'-sulfo-2',6'-dimethyl-5'-aminomethylphenyl)aminoanthraquinone, 1-amino-2,7-disulfo-4-[3'-sulfo-2',6'-dimethyl-5'-(N-methylamino)-methylphenyl]aminoanthraquinone, 1-amino-2,7-disulfo-4-[2',6'-dimethyl-5'-(N-methylamino)methylphenyl]aminoanthraquinone, 1-amino-2,5-disulfo-4-(2'-sulfo-4'-methyl-3'-aminomethylphenyl)aminoanthraquinone, 1-amino-2,8-disulfo-4-(4'-methyl-3'-aminomethylphenyl)aminoanthraquinone, 1-amino-2,5,8-trisulfo-4-(2',6'-dimethyl-3'-aminomethylphenyl)aminoanthraquinone, 1-amino-2,7-disulfo-4-[4'-methoxy-3'-(N-methylamino)methylphenyl]aminoanthraquinone, 1-amino-2,5-disulfo-4-[2'-sulfo-4'-methoxy-3'-(N-methylamino)methylphenyl]aminoanthraquinone, 1-amino-2,8-disulfo-4-(2'-sulfo-3' -aminomethylphenyl)aminoanthraquinone, 1-amino-2,7-disulfo-4-(2'-sulfo-4'-methoxy-3'-aminomethylphenyl)aminoanthraquinone, 1-amino-2,5-disulfo-4-(3'-sulfo-4'-aminophenyl)aminoanthraquinone, 1-amino-2,5-disulfo-4-(3'-sulfo-6'-methyl-5'-aminophenyl)aminoanthraquinone, 1-amino-2,7-disulfo-4-(β-aminoethyl)aminoanthraquinone, 1-amino-2,6-disulfo-4-[β-(N-methylamino)ethyl]aminoanthraquinone, 1-amino-2-sulfo-4-[3'-(4''-sulfo-3''-aminophenyl)sulfonylamidosulfonylphenyl]aminoanthraquinone, 1-amino-2,6-disulfo-4-[4'-(4''-aminophenyl)sulfonylamidosulfonylphenyl]aminoanthraquinone and 1-amino-2-sulfo-4 -[3'-(4''-aminophenyl)sulfonylamidosulfonylphenyl]aminoanthraquinone.

The starting compounds of the formula (7) are in some instances known; however, the compounds where R is alkyl or alkoxy have not been described before. Therefore compounds of the formula (7) where R is alkyl of 1 to 4 carbon atoms or alkoxy of 1 to 4 carbon atoms likewise form part of the subject-matter of the present invention.

The compounds of the formula (7) can be prepared by reducing a nitro compound of the formula (10)

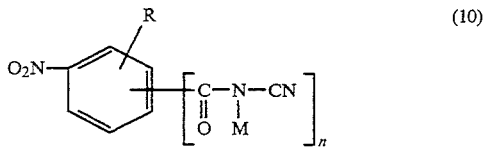 (10)

where R, M and n are each as defined above, in a conventional manner, preferably catalytically in aqueous solution or suspension, to the compound of the formula (7) where $R^2$ is hydrogen. The introduction of an alkyl group (in the case of $R^2$ being alkyl) can then be carried out subsequently with the aid of an alkylating agent, such as a dialkyl sulfate, in a conventional manner similarly to known procedures.

The compounds of the formula (10) where R is alkyl of 1 to 4 carbon atoms or alkoxy of 1 to 4 carbon atoms and n is 1 or 2, or where R is hydrogen and n is 2 have likewise not been described before and thus form part of the subject-matter of the present invention.

The starting compounds of the formula (10), which, as mentioned earlier, are in some instances already known (see J. Org. Chem. 31, 959–961 (1966) and Chem. Ind. (London) 1963, 1559+1560) can be prepared in a manner similar to these literature-described methods, for example by reacting the acid chlorides of the formula (11)

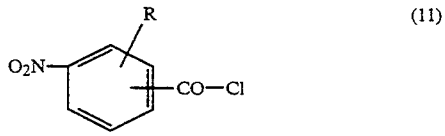 (11)

where R is as defined above, with cyanamide or a salt of cyanamide in aqueous solution or suspension at a temperature between 0° and 20° C. and at a pH maintained between 7 and 11.

Starting compounds of the formula (7) include for example 2-amino-N'-cyanobenzamide, 3-amino-N'-cyanobenzamide, 4-amino-N'-cyanobenzamide, 5-amino-1,3-di(N'-cyanocarboxamido)benzene, 3-amino-4-methoxy-N'-cyanobenzamide and 3-methyl-4-amino-N'-cyanobenzamide.

The separation of the dyes of the formula (1) prepared according to the invention—hereinafter termed "dyes (1)"—from the synthesis batches is effected according to generally known methods either by precipitating from the reaction medium by means of electrolytes, for example sodium chloride or potassium chloride, or by evaporating the reaction solution, for example by spray-drying, in which case a buffer substance may be added to this reaction solution. They have fiber-reactive properties and very good dye properties. They can therefore be used for dyeing and printing hydroxy- and/or carboxamido-containing material, in particular fiber material, but also leather. Similarly, the as-synthesized solutions of compounds according to the invention may be used directly as liquid dyes, optionally after addition of a buffer substance and optionally after concentrating.

The present invention therefore also provides for the use of the dyes (1) for dyeing and in particular printing hydroxy- and carboxamido-containing materials, i.e. processes for applying the dyes (1) to these substrates. The materials are preferably employed in the form of fiber materials, in particular textile fibers, such as yarns, wound packages and fabrics.

Hydroxy-containing materials are natural or synthetic hydroxy-containing materials, for example cellulose fiber materials, including the form of paper, or regenerated products thereof, and polyvinyl alcohols. Cellulose fiber materials are preferably cotton but can also be other vegetable fibers, such as linen, hemp, jute and ramie fibers, while regenerated cellulose fibers are for example staple viscose and filament viscose.

Carboxamido-containing materials include for example synthetic and natural polyamides and polyurethanes, in particular in the form of the fibers, for example wool and other animal hairs, silk, leather, nylon-6,6, nylon-6, nylon-11 and nylon-4.

The dyes (1) can be applied to and fixed on said substrates, in particular on the fiber materials mentioned, by the techniques known for water-soluble dyes, in particular for fiber-reactive dyes. For instance, on cellulose fibers they produce dyeings in good color yields. The dyeing is carried out at temperatures between 40° and 105° C., optionally at temperatures up to 130° C. under superatmospheric pressure, and optionally in the presence of customary dyeing assistants, from an aqueous bath. One possible procedure is to introduce the material into the hot bath, gradually heat the bath to the desired dyeing temperature, and complete the dyeing process at that temperature. The neutral salts which speed up the exhaustion of the dye can also if desired not be added to the bath until the actual dyeing temperature has been reached.

Padding processes likewise produce dyeings on cellulose fibers in excellent color yields, fixation being possible in a conventional manner by hatching at room temperature or elevated temperature, for example at up to 60° C., by steaming or using dry heat.

Similarly, the conventional printing processes for cellulose fibers—which are preferably carried out in a single phase, for example by printing with a print paste containing sodium bicarbonate or another acid-binding agent and the dye (1) and subsequent steaming at from 100° to 103° C., or can be carried out in two phases, for example by printing with a neutral or weakly acid print paste containing the dye (1) and subsequent fixation either by passing the printed material through a hot electrolyte-containing alkaline bath or by overpadding with an alkaline electrolyte-containing padding liquor and subsequent hatching of this treated material or subsequent steaming or subsequent treatment with dry heat—produce strong prints with well defined contours and a clear white ground. Variable fixing conditions have only little effect on the outcome of the prints. Not only in dyeing but also in printing the degrees of fixation obtained with the dyes (1) are very high. The hot air used in dry heat fixing by the customary thermofix processes has a temperature of from 120° to 200° C. In addition to customary steam at from 101° to 103° C. it is also possible to use superheated steam or high-pressure steam having temperatures of up to 160° C.

The acid-binding agents responsible for fixing the dyes to the cellulose fibers include for example water-soluble basic salts of alkali metals and of alkaline earth metals of inorganic or organic acids, and compounds which are capable of releasing alkali when hot. Of particular suitability are the alkali metal hydroxides and alkali metal salts of weak to medium inorganic or organic acids, the preferred alkali metal compounds being the sodium and potassium compounds. These acid-binding agents include for example sodiumhydroxide, potassiumhydroxide, sodium carbonate, sodium bicarbonate, potassium carbonate, sodium formate, sodium dihydrogenphosphate and disodium hydrogenphosphate.

Treating the dyes (1) with the acid-binding agents with or without heating bonds the dyes chemically to the cellulose fiber; especially the dyeings on cellulose, after they have been given the usual aftertreatment of rinsing to remove unfixed dye portions, show excellent wet fastness properties, in particular since the unfixed dye portions are readily washed off because of their good cold water solubility.

The dyeings of polyurethane and polyamide fibers are customarily carried out from an acid medium. The dyebath may contain for example acetic acid and/or ammonium sulfate and/or acetic acid and ammonium acetate or sodium acetate to bring it to the desired pH. To obtain a dyeing of acceptable levelness it is advisable to add customary leveling assistants, for example based on a reaction product of cyanuric chloride with three times the molar amount of an aminobenzenesulfonic acid or aminonaphthalenesulfonic acid or based on a reaction product of for example stearylamine with ethylene oxide. In general the material to be dyed is introduced into the bath at a temperature of about 40° C. and agitated therein for some time, the dyebath is then adjusted to the desired weakly acid, preferably weakly acetic acid, pH, and the actual dyeing is carried out at a temperature between 60° and 98° C. However, the dyeings can also be carried out at the boil or at temperatures of up to 120° C. (under superatmospheric pressure).

The dyeings and prints prepared using the dyes (1) of the invention have high color strength and good light fastness properties and good wet fastness properties, such as wash, fulling, water, seawater, crossdyeing and perspiration fastness properties, but also good fastness to pleating, hot pressing and rubbing. Attention has to be drawn in particular to their alkaline perspiration light fastness and the good wet light fastness of dyeings wetted with tap water.

The Examples which follow illustrate the invention. The compounds described by means of a formula are shown in the form of the free acid; generally they are prepared and isolated in the form of their alkali metal salts and used for dyeing in the form of their salts. In the same way the starting compounds mentioned in the form of the free acid in the Examples which follow, in particular Table Examples, can be used in the synthesis as such or in the form of their salts, preferably alkali metal salts, such as sodium or potassium salts.

Parts and percentages are by weight, unless otherwise stated. Parts by weight bear the same relation to parts by volume as the kilogram to the liter.

The visible absorption maxima ($\lambda_{max}$) reported for the compounds of the invention were determined on aqueous solutions of their alkali metal salts. In the Table Examples the $\lambda_{max}$ values are shown in parentheses in the hue column; the wavelength is given in run.

The $^{13}$C-NMR analyses were carried out in dimethyl sulfoxide and using tetramethylsilane as internal standard, unless otherwise stated.

EXAMPLE A a) 584 parts of pulverulent 3-nitrobenzoyl chloride are suspended in 15,000 parts of water; 157.5 parts of cyanamide are added, followed by 2520 parts by volume of 10% aqueous strength sodium hydroxide solution to set the pH between 8 and 8.5 and keep it there during the reaction, which is carried out at 10° C. The resulting 3-nitro-N-cyanobenzamide is salted out with sodium chloride, filtered off and dried.

b) 4-Nitro-N-cyanobenzamide can be prepared in the same way (as the alkali metal salt) starting from 4-nitrobenzoyl chloride.

EXAMPLE B 744 parts of 1-nitrobenzene-3,5-dicarbonyl chloride are suspended in 15 parts of water, the suspension is admixed with 315 parts of cyanamide, and 10% strength sodium hydroxide solution is used to set a pH between 8 and 8.5 and keep it there during the reaction, which is carried out at a temperature of about 10° C. Then the synthesized compound 1-nitrobenzene-3,5-di(N-cyanocarboxamide) is isolated by precipitating at pH 1. It is a solid substance.

The following analytical values were obtained:
Elemental analysis: calculated: C 40.8%, H 2.1%, N 29.8%; found: C 35.3%, H 2.1%, N 29.5%.

$^{13}$C-NMR analysis (in ppm): 115.7, 125.5, 133.7, 136.7, 147.8, 168.8.

EXAMPLE C

4-Nitro-3-methyl-N-cyanobenzamide is prepared as described in Example A using an equivalent amount of 4-nitro-3-methylbenzoyl chloride.

The compound is obtained as a solid substance. The following analytical values were obtained:
Elemental analysis: calculated: C 47.5%, H 2.7%, N 18.5%; found: C 43.7%, H 2.8%, N 17.05%.

$^{13}$C-NMR analysis (in ppm): 19.5, 122.0, 123.7, 126.8, 131.9, 132.3, 142.9, 149.8, 172.7.

EXAMPLE D

3-Nitro-4-methoxy-N-cyanobenzamide is prepared as described in Example A using an equivalent amount of 3-nitro-4-methoxybenzoyl chloride. The product is obtained as a solid substance; it has the following physical characteristics:

$^{13}$C-NMR analysis (in ppm): 56.90, 113.4, 122.12, 124.63, 131.3, 134.0, 138.6, 153.47, 172.2.

EXAMPLE E 250 parts of 3-nitro-N-cyanobenzamide (Example A) are suspended in 2500 parts of water at pH 7.5; 1.5 parts of a palladium/activated carbon catalyst (containing 10% of Pd) are added, and the product is hydrogenated for two hours at 20° to 30° C. and 50 bar hydrogen. The catalyst is then filtered off, the filtrate is adjusted with concentrated aqueous hydrochloric acid to pH 4, and the precipitated 3-amino-N'-cyanobenzamide is filtered off and dried.

It shows a solid substance which does not melt below 250° C.

EXAMPLE F

4-Amino-N'-cyanobenzamide is prepared as described in Example E starting from the isomeric 4-nitro- N-cyanoamidobenzamide. The compound is obtained as a solid substance which does not melt below 250° C.

EXAMPLE G

3-Amino-4-methoxy-N'-cyanobenzamide is prepared by reducing 3-nitro-4-methoxy-N-cyanobenzamide (Example D) as described in Example E. A solid substance is obtained, which does not melt below 250° C. The following analytical values were obtained:

Elemental analysis: calculated: C 56.6%, H 4.7%, N 22.0%; found: C 49.3%, H 5.2%, N 19.0%.

$^{13}$C-NMR analysis (in ppm): 55.82, 109.9, 110.6, 113.5, 117.9, 123.3, 137.4, 150.8, 167.4.

EXAMPLE H

4-Amino-3-methyl-N'-cyanobenzamide is prepared by reducing 4-nitro-3-methyl-N-cyanobenzamide (Example C) as described in Example E. The product is isolated as a solid substance.

EXAMPLE 1

To a 0° C. solution of 20.5 parts of 1-amino-4-(3'-amino-2',4',6'-trimethylphenyl)aminoanthraquinone-2,5'-disulfonic acid in 250 parts of water are added 7.7 parts of 2,4,6-trichloro-s-triazine; during the reaction at 0° C. which takes about 1 hour, a pH of 4 is maintained with aqueous sodium hydroxide solution. Then 6.6 parts of 4-amino-N'-cyanobenzamide are added, the temperature of the batch is heated to 10° C., and the second reaction is carried out at a pH of 6.5 in the course of two hours. The anthraquinone compound of the invention is isolated in a conventional manner by salting out with sodium chloride. Written in the form of the free acid it has the formula and shows very good dye properties. Applied to the materials mentioned in the description, in particular cellulose fiber materials, such as cotton, by the techniques customary in the art for fiber-reactive dyes it produces strong, fast dyeings and prints in brilliant blue shades having good fastness properties.

EXAMPLE 2

Example 1 is repeated with the equivalent mount of 1-amino-4-(2'-methyl-3'-aminophenyl)aminoanthraquinone-2,5'-disulfonic acid, affording the novel anthraquinone dye of the formula

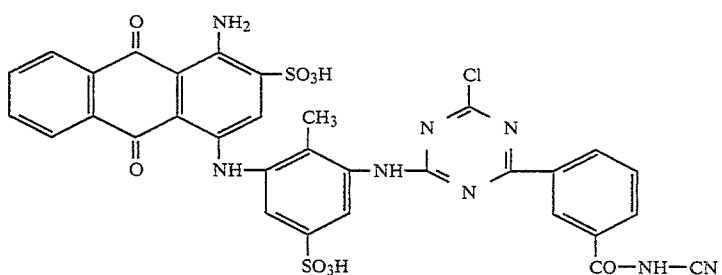

($\lambda_{max}$ = 612 nm)

in the form of the sodium salt. Applied to and fixed on the materials mentioned in the description, in particular cellulose fiber materials, by the techniques customary in the art for fiber-reactive dyes it produces strong, fast, brilliant blue dyeings and prints.

EXAMPLE 3

To a solution of 51 parts of 1-amino-4-(3'-amino-2',4',6'-trimethylphenyl)aminoanthraquinone-2,4'-disulfonic acid in 350 parts of water at 0° C. are gradually added, at that temperature and at a pH of 5, 10 parts by volume of cyanuric fluoride; during the reaction the pH of 5 is maintained with aqueous 2 N sodium hydroxide solution. Then 16 parts of 3-amino-N'-cyanobenzamide are added, the temperature of the batch is raised to 5°–10° C. and the reaction is carried out at a pH of 6 in the course of 3 hours.

The anthraquinone dye of the invention is salted out with sodium chloride and isolated in the form of the sodium salt as a blue powder that contains sodium chloride. Written in the form of the free acid it has the formula

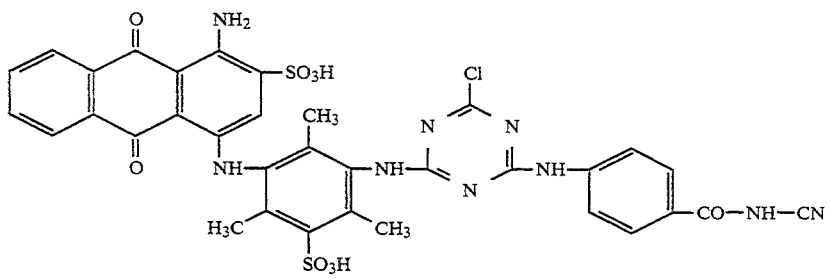

($\lambda_{max}$ = 584 nm)

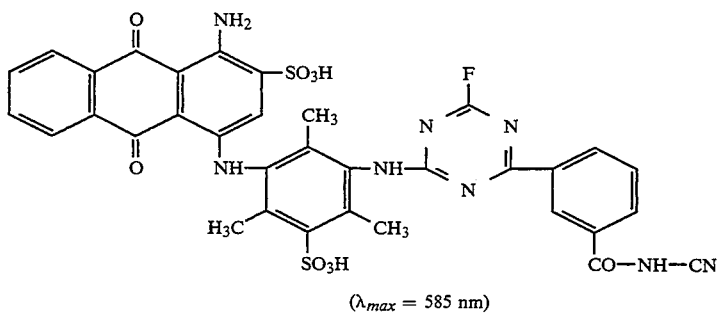

(λ$_{max}$ = 585 nm)

shows very good dye properties and dyes for example cotton by the application techniques customary in the art for fiber-reactive dyes in fast, brilliant blue shades.

EXAMPLE 4

A 0° C. solution of 65 parts of 1-amino-4-(3'-aminophenyl)aminoanthraquinone-2,4'-disulfonic acid in 250 parts of water is slowly admixed with 13.5 parts by volume of cyanuric fluoride while a pH of 5 is maintained. The batch is subsequently stirred for about a further 10 minutes. Then 24.8 parts of 4-amino-N'-cyanobenzamide are added, the temperature of the batch is raised to 10° C., the reaction is carried out in the course of about 3 hours while a pH of between 6 and 6.5 is maintained. The anthraquinone dye of the invention is isolated from the synthesis solution by salting out with sodium chloride. Written in the form of the free acid it has the formula

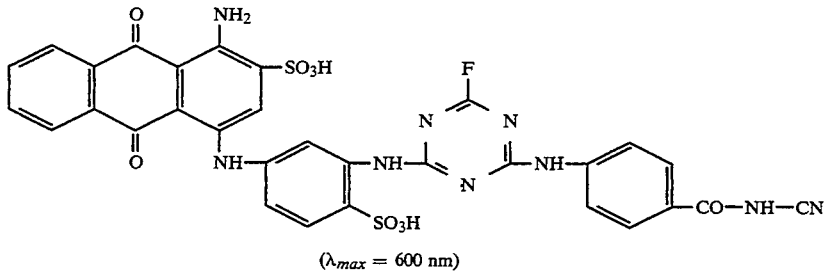

(λ$_{max}$ = 600 nm)

and applied to the materials mentioned in the description, in particular cellulose fiber materials, by the known techniques for fiber-reactive dyes produces deep blue shades having good fastness properties.

EXAMPLES 5 to 22

The Table Examples which follow describe further novel anthraquinone dyes conforming to a formula (A)

$$\text{[AC]}\!-\!\underset{\text{NH}}{|}\!-\!\text{B}\!-\!\underset{\text{R}^1}{\text{N}}\!-\!\underset{\text{N}}{\overset{\text{Hal}}{\underset{\|}{\text{C}}}}\!\underset{\text{N}}{\overset{\text{N}}{\underset{\|}{\text{C}}}}\!-\!\text{NH}\!-\!\text{E} \quad (A)$$

in terms of their components (the anthraquinone radical AC conforming to the formula (a)

(a)

the bivalent radical B, the halogen atom chlorine or fluorine, and the cyanobenzamide radical E). They are preparable in a manner according to the invention, for example analogously to one of the above-described examples, using an anthraquinone compound conforming to the formula AC—NH—B—NHR$^1$, cyanuric chloride or cyanuric fluoride, and a cyanamidocarbonylaniline compound conforming to the formula H$_2$N—E. These novel anthraquinone dyes have very good fiber-reactive dye properties and dye the materials mentioned in the description, in particular cellulose fiber materials, such as cotton, in the hue reported in the respective Table Example (for cotton) in high color strength and good fastness properties.

| | Anthraquinone dye of the formula (A) | | | | | |
|---|---|---|---|---|---|---|
| Ex. | AC | B | R$^1$ | Hal | E | Hue |
| 5 | 1-Amino-2-sulfo-anthraquinon-4-yl | 5-Sulfo-2,4,6-trimethyl-1,3-phenylene | H | Chlorine | 4-(Cyanamidocarbonyl)phenyl | blue (585) |
| 6 | 1-Amino-2-sulfo-anthraquinon-4-yl | 5-Sulfo-2,4,6-trimethyl-1,3-phenylene | H | Chlorine | 2-Methyl-4-(cyanamidocarbonyl)phenyl | blue (613) |

-continued

| Ex. | AC | B | R¹ | Hal | E | Hue |
|---|---|---|---|---|---|---|
| 7 | 1-Amino-2-sulfo-anthraquinon-4-yl | 5-Sulfo-2,4,6-trimethyl-1,3-phenylene | H | Chlorine | 2-Methoxy-5-cyanamidocarbonyl)phenyl | blue (584) |
| 8 | 1-Amino-2,7-disulfo-anthraquinon-4-yl | 1,4-Cyclohexylene | H | Chlorine | 2-Methoxy-5-cyanamidocarbonyl)phenyl | blue |
| 9 | 1-Amino-2,7-disulfo-anthraquinon-4-yl | 1,4-Cyclohexylene | H | Chlorine | 3-(Cyanamidocarbonyl)-phenyl | blue |
| 10 | 1-Amino-2-sulfoanthraquinon-4-yl | 6-Sulfo-4-methyl-1,2-phenylene | CH₃ | Chlorine | 4-(Cyanamidocarbonyl)-phenyl | blue |
| 11 | 1-Amino-2-sulfoanthraquinon-4-yl | 6-Sulfo-4-methyl-1,2-phenylene | CH₃ | Chlorine | 2-Methoxy-5-(cyanamidocarbonyl)phenyl | blue |
| 12 | 1-Amino-2-sulfoanthraquinon-4-yl | 3-Sulfo-1,4-phenylene | CH₃ | Chlorine | 3-(Cyanamidocarbonyl)-phenyl | blue |
| 13 | 1-Amino-2-sulfoanthraquinon-4-yl | 3-Sulfo-1,4-phenylene | CH₃ | Chlorine | 4-(Cyanamidocarbonyl)-phenyl | blue |
| 14 | 1-Amino-2-sulfoanthraquinon-4-yl | 5-Sulfo-2-methyl-1,3-phenylene | H | Fluorine | 3-(Cyanamidocarbonyl)-phenyl | blue (612) |
| 15 | 1-Amino-2-sulfoanthraquinon-4-yl | 5-Sulfo-2,4,6-trimethyl-1,3-phenylene | H | Fluorine | 3-(Cyanamidocarbonyl)-phenyl | blue (584) |
| 16 | 1-Amino-2-sulfoanthraquinon-4-yl | 5-Sulfo-2,4,6-trimethyl-1,3-phenylene | H | Fluorine | 2-Methoxy-5-(cyanamidocarbonyl)phenyl | blue (584) |
| 17 | 1-Amino-2,7-disulfo-anthraquinon-4-yl | 1,4-Cyclohexylene | H | Fluorine | 2-Methoxy-5-(cyanamidocarbonyl)phenyl | blue |
| 18 | 1-Amino-2,7-disulfo-anthraquinon-4-yl | 1,4-Cyclohexylene | H | Fluorine | 3-(Cyanamidocarbonyl)-phenyl | blue |
| 19 | 1-Amino-2-sulfo-anthraquinon-4-yl | 6-Sulfo-4-methyl-1,2-phenylene | Methyl | Fluorine | 4-(Cyanamidocarbonyl)-phenyl | blue |
| 20 | 1-Amino-2-sulfo-anthraquinon-4-yl | 3-Sulfo-1,4-phenylene | CH₃ | Fluorine | 3-(Cyanamidocarbonyl)-phenyl | blue |
| 21 | 1-Amino-2-sulfo-anthraquinon-4-yl | 3-Sulfo-1,4-phenylene | CH₃ | Fluorine | 4-(Cyanamidocarbonyl)-phenyl | blue |
| 22 | 1-Amino-2-sulfo-anthraquinon-4-yl | 3-Sulfo-1,4-phenylene | CH₃ | Fluorine | 2-Methoxy-5-(cyanamidocarbonyl)phenyl | blue |

What is claimed is:

1. An anthraquinone compound conforming to the formula (1a)

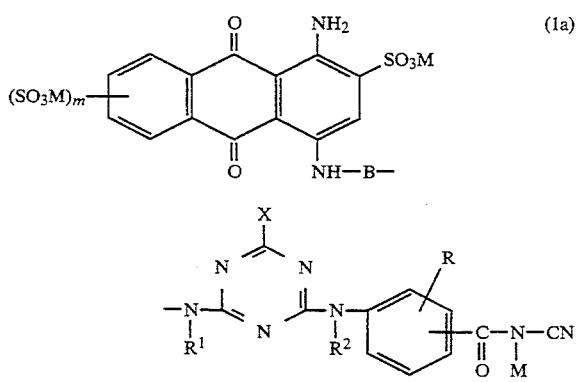

wherein
$R^1$ is hydrogen or alkyl of 1 to 4 carbon atoms,
$R^2$ is hydrogen or alkyl of 1 to 4 carbon atoms,
M is hydrogen or an alkali metal or the mole equivalent of an alkaline earth metal,
m is zero, 1 or 2, and when m is zero, the missing $SO_3M$ group is replaced by a hydrogen,
B is phenylene which is substituted by 1 or 2 sulfo groups and 2 or 3 $C_1$-$C_4$-alkyls or 2 or 3 $C_1$-$C_4$-alkoxies; or is phenylenealkylene or alkylenephenylene wherein the alkylene radicals have 1 to 4 carbon atoms and the phenylene radicals are substituted by 1 or 2 sulfo groups and 2 or 3 $C_1$-$C_4$-alkyls or 2 or 3 $C_1$-$C_4$-alkoxies; or is a radical of the formula -phen-D-phen- in which each phen is identical to or different from the other and is a phenylene substituted as mentioned above and D is a direct bond or a group of the formula —NH—, —O—, —SO₂—, —CO—NH—, —NH—CO—, —SO₂—NH—, —NH—SO₂— and —SO₂—NH—SO₂—,
X is chlorine or fluorine, and
R is hydrogen, $C_1$-$C_4$-alkyl or $C_1$-$C_4$-alkoxy.

2. The anthraquinone compound as claimed in claim 1, wherein P is phenylene which is substituted by 1 or 2 sulfo groups and 2 or 3 $C_1$-$C_4$-alkyls or 2 or 3 $C_1$-$C_4$-alkoxies.

3. The anthraquinone compound as claimed in claim 1, wherein B is phenylene which is substituted by one sulfo group and three $C_1$-$C_4$-alkyls or three $C_1$-$C_4$-alkoxies.

4. The anthraquinone compound as claimed in claim 1, conforming to the formula (5)

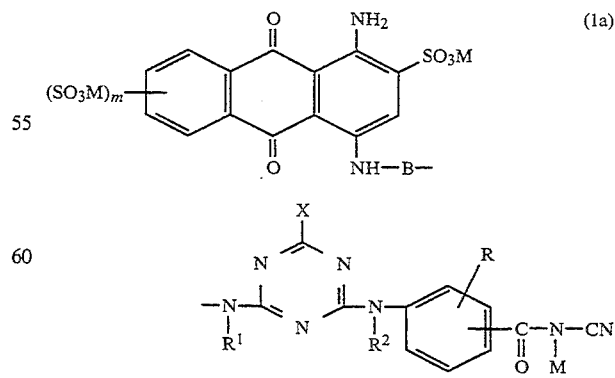

where M, R and X are each defined in claim 1.

5. An anthraquinone compound as claimed in claim 1, wherein R is $C_1$-$C_4$-alkyl or $C_1$-$C_4$-alkoxy.

6. An anthraquinone compound as claimed in claim 1, wherein m is zero.

7. An anthraquinone compound as claimed in claim 1 of the formula

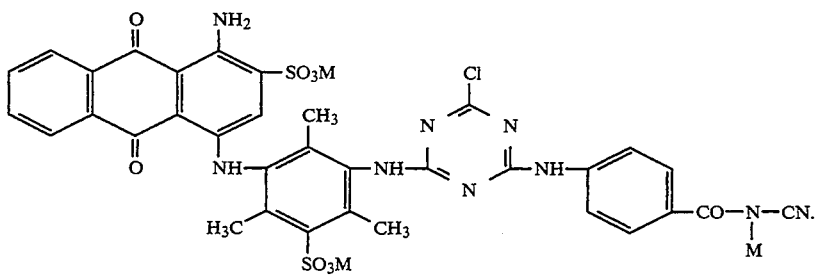

8. An anthraquinone compound as claimed in claim 1 of the formula

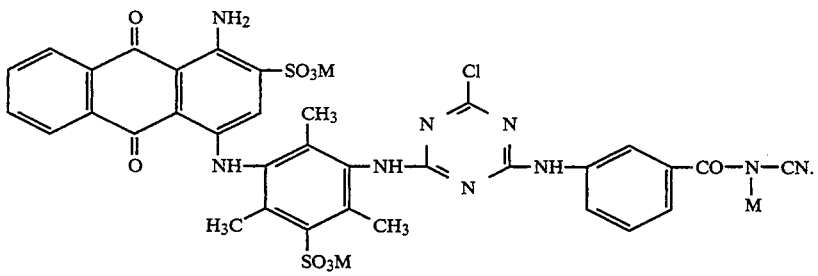

9. An anthraquinone compound as claimed in claim 1 of the formula

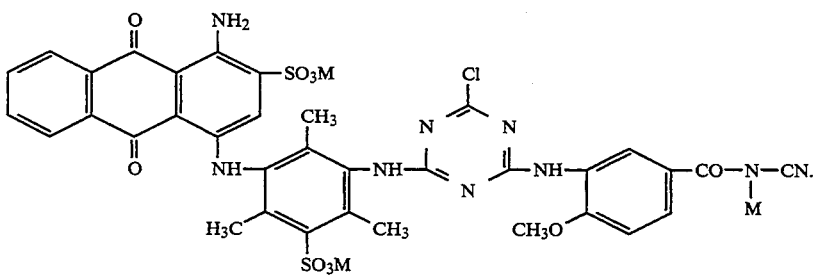

where M is as defined in claim 1.

10. An anthraquinone compound as claimed in claim 1 of the formula

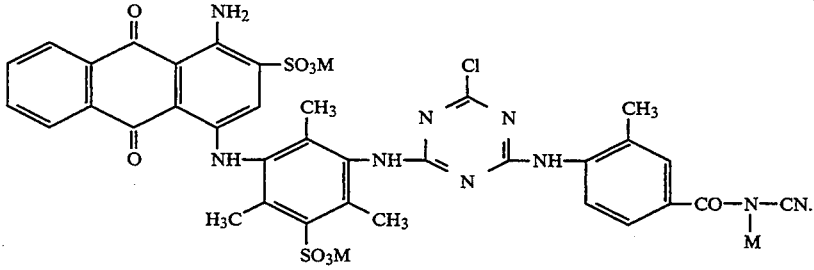

11. A compound conforming to the formula

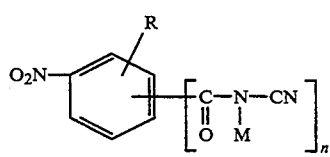

where
R is alkyl of 1 to 4 carbon atoms or alkoxy of 1 to 4 carbon atoms,
M is hydrogen or an alkali metal or the mole equivalent of an alkaline earth metal, and
n is 1 or 2.

12. A compound conforming to the formula (7)

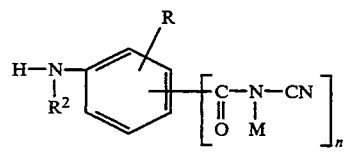

(7)

where
$R^2$ is hydrogen or alkyl of 1 to 4 carbon atoms,
R is alkyl of 1 to 4 carbon atoms or alkoxy of 1 to 4 carbon atoms,
M is hydrogen or an alkali metal or the mole equivalent of an alkaline earth metal and
n is 1 or 2.

* * * * *

UNITED STATES PATENT AND TRADEMARK OFFICE
CERTIFICATE OF CORRECTION

PATENT NO. : 5,430,147
DATED : July 4, 1995
INVENTOR(S) : Dannheim et al

It is certified that error appears in the above-indentified patent and that said Letters Patent is hereby corrected as shown below:

In column 18, line 50 (line 3 of claim 4), please delete the formula and insert the following formula (5):

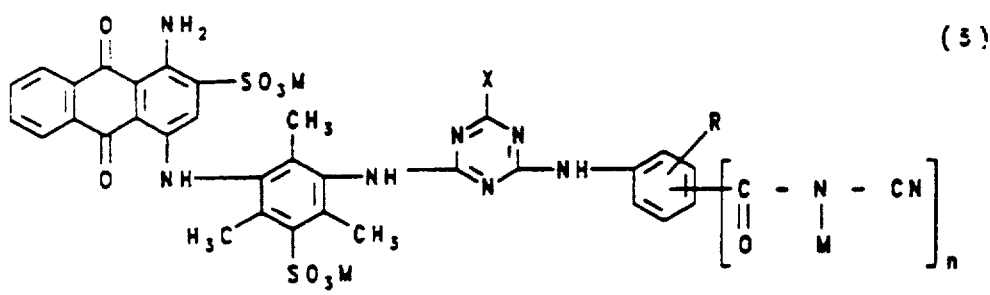

Signed and Sealed this

Fourteenth Day of November, 1995

Attest:

BRUCE LEHMAN

Attesting Officer

Commissioner of Patents and Trademarks